(12) United States Patent
Stubenrauch et al.

(10) Patent No.: US 9,671,394 B2
(45) Date of Patent: Jun. 6, 2017

(54) METHOD FOR THE DETECTION OF FREE BINDING PARTNER OF A MULTISPECIFIC BINDER

(71) Applicant: Hoffmann-La Roche Inc., Nutley, NJ (US)

(72) Inventors: Kay-Gunnar Stubenrauch, Penzberg (DE); Uwe Wessels, Penzberg (DE)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 14/308,539

(22) Filed: Jun. 18, 2014

(65) Prior Publication Data

US 2015/0072359 A1   Mar. 12, 2015

Related U.S. Application Data

(63) Continuation of application No. PCT/EP2012/075991, filed on Dec. 18, 2012.

(30) Foreign Application Priority Data

Dec. 19, 2011 (EP) .................................... 11194350

(51) Int. Cl.
*G01N 33/543* (2006.01)
*G01N 33/53* (2006.01)

(52) U.S. Cl.
CPC ....... *G01N 33/54306* (2013.01); *G01N 33/53* (2013.01); *G01N 33/5306* (2013.01); *G01N 33/54393* (2013.01)

(58) Field of Classification Search
None
See application file for complete search history.

(56) References Cited

U.S. PATENT DOCUMENTS 4,699,880 A   10/1987 Goldstein et al.

FOREIGN PATENT DOCUMENTS

| CN | 102207054 A | 10/2011 |
|---|---|---|
| EP | 0 962 771 A1 | 8/1999 |
| JP | S56-128722 | 8/1981 |
| WO | 95/04931 A1 | 2/1995 |
| WO | 01/36972 A2 | 5/2001 |
| WO | 2005/022150 A2 | 3/2005 |
| WO | 2008/060777 A2 | 5/2008 |
| WO | 2006/096697 A2 | 6/2009 |

OTHER PUBLICATIONS

Berkova et al., "Development of an Enzyme Immunoassay for the Measurement of Human Tumuor Necrosis Factor-x (hTNF-x) Using Bispecific Antibodies to hTNF-x and Horseradish Peroxidase" Biotechnology and Applied Biochemistry 23(2):163-171 (Apr. 1, 1996).
Bruynck et al., "Characterisation of a humanised Bispecific Monoclonal Antibody for Cancer Therapy" British Journal of Cancer 67(3):436-440 (Mar. 1, 1993).
Chen et al., "Rapid Detection of Hepatitis B Virus Surface Antigen by an Agglutination Assay Meiated by a Bispecific Diabody Againt Both Human Erythrocytes and Hepatitis B Virus Surface Antigen" Clinical and Vaccine Immunology 14(6):720-725 (Apr. 18, 2007).
Doppalapudi et al., "Chemical Generation of Bisspecific Antibodies" PNAS 107(52):22611-22616 (Dec. 28, 2010).
European Search Report for Application No. EP11194350.
Guttikonda et al., "Monospecific and bispecific antibodies against *E. coli* O157 for diagnostics" Journal of Immunological Methods 327:1-9 ( 2007).
Liu et al., "Bispecific monoclonal antibodies against a viral and an enzyme; utilities in ultrasensitive virus ELISA and phage display technology" Journal of Immunological Methods 274:115-127 ( 2003).
PCT Written Opinion of the International Searching Authority for PCT/EP2012/075991.
Porter et al., "An Electro-Active System of Immuno-Assay (EASI Assay) Utilising Self Assembled monolayer Modified Electrodes" Biosensors & Bioelectronics 16(9-12):875-885 (Dec. 1, 2001).
Reinartz et al., "Bispecific Multivalent Antibody Studies by Real-Time Interaction Analysis for the Development of an Antigen-Inhibittion Enzyme-Linked Immunosorbent Assay" Annlyst 121(6):767-771 (Jun. 1, 1996).
European Search Report for Application No. EP11194350, 2012 mailing date.
Doppalapudi, V. et al., "Chemical Generation of Bispecific Antibodies" Proceedings of the National Academy of Sciences 107(52):22611-22616 (Dec. 28, 2010).
CN102207504A English Abstract, p. 1 ( Oct. 5, 2011).
English translation of CN Office Action, p. 1, 2011.

*Primary Examiner* — Jacob Cheu
(74) *Attorney, Agent, or Firm* — Frank JN Berendt

(57) ABSTRACT

Herein is reported a method for the detection of free antigen of a multispecific antibody in a sample, whereby the antigen to be detected can be specifically bound by a first binding site of the multispecific antibody, comprising the step of incubating a sample comprising free antigen and multispecific antibody with an anti-idiotypic antibody that specifically binds to a second binding site of the multispecific antibody, which is different from the first binding site, and thereby depleting the multispecific antibody from the sample.

26 Claims, 7 Drawing Sheets

METHOD FOR THE DETECTION OF FREE BINDING PARTNER OF A MULTISPECIFIC BINDER

CROSS-REFERENCE TO RELATED APPLICATIONS

This application is a continuation of International Application PCT/EP2012/075991, filed Dec. 18, 2012, which claims the benefit of European Patent Application No. 11194350.2, filed Dec. 19, 2011, all of which are hereby incorporated by reference in their entirety.

FIELD OF THE INVENTION

The current invention is directed to a method for the detection of free, i.e. non-complexed, binding partner which can be specifically bound by a multispecific binder in a sample, wherein binding partner bound to the multispecific binder is depleted from the sample prior to the detection of the free binding partner.

BACKGROUND OF THE INVENTION

Standard solid-phase immunoassays with antibodies involve the formation of a complex between an antibody adsorbed/immobilized on a solid phase (capture antibody), the antigen, and an antibody to another epitope of the antigen conjugated with an enzyme or detectable label (tracer antibody). In the assay, a sandwich is formed: solid phase/capture antibody/antigen/tracer antibody. In the reaction catalyzed by the sandwich among other things the activity of the antibody-conjugated enzyme is proportional to the antigen concentration in the incubation medium. Anti-idiotypic antibody assays are mentioned, for example, in U.S. Pat. No. 5,219,730; WO 87/002778; EP 0 139 389; and EP 0 170 302. Wadhwa, M., et al. (J. Immunol. Methods 278 (2003) 1-17) report strategies for the detection, measurement and characterization of unwanted antibodies induced by therapeutic biologicals. A method for producing anti idiotypic antibodies is reported in EP 1 917 854.

Chen, Y.-P., et al. (Clin. Vac. Immunol. 14 (2007) 720-725) report the rapid detection of hepatitis B virus surface antigen by an agglutination assay mediated by a bispecific diabody against both human erythrocytes and hepatitis B virus surface antigen. The characterisation of a humanised bispecific monoclonal antibody for cancer therapy is reported by Bruynck, A., et al. (J. Cancer 67 (1993) 436-440). In WO 2006/096697 methods for determining the bivalency of protein and antibody therapeutics is reported.

SUMMARY OF THE INVENTION

Herein is reported a method for the detection of the presence and/or for the determination of the amount of a free, i.e. non-complexed, binding partner that can be specifically bound by at least one binding specificity of a multispecific binder. It has been found that it is advantageous to deplete the binding partner that is specifically bound by the multispecific binder, i.e. the binding partner-multispecific binder-complex, from the sample prior to the determination of the presence or the amount of free binding partner. According to the methods as reported herein is the depletion of the multispecific binder achieved by incubating the sample with an monospecific binder that specifically binds to one binding specificity of the multispecific binder, whereby the monospecific binder specifically binds to a binding specificity of the multispecific binder that does not bind to the binding partner to be determined (see FIG. 2).

One aspect as reported herein is a method for the in vitro determination of the presence and/or the amount of a binding partner (antigen, target, analyte), which can be specifically bound by a first binding specificity of a multispecific binder, wherein binding partner bound to the multispecific binder is depleted prior to the detection of the binding partner by incubating the sample with a monospecific binder specifically binding to a second binding specificity of the multispecific binder.

In one embodiment the binding partner to be detected is non-complexed binding partner or free binding partner.

Thus, one aspect as reported herein is an in vitro method for the determination of the presence and/or the amount of a binding partner of a multispecific binder, whereby the binding partner can be specifically bound by a first binding specificity of the multispecific binder, comprising the step of:

incubating a sample comprising binding partner and multispecific binder with a monospecific binder that specifically binds to a second binding specificity of the multispecific binder which is different from the first binding specificity.

In one embodiment the method comprises the steps of:

incubating a sample comprising binding partner and multispecific binder with an monospecific binder that specifically binds to a second binding specificity of the multispecific binder which is different from the first binding specificity, and determining the amount of the binding partner in the multispecific binder-depleted sample.

In one embodiment the method comprises the step of:

incubating a sample comprising binding partner and multispecific binder with an monospecific binder that specifically binds to a second binding specificity of the multispecific binder which is different from the first binding specificity, depleting the monospecific binder-multispecific binder-complex from the sample prior to the determination of the presence or the amount of free binding partner, and determining the amount of the binding partner in the multispecific binder-depleted sample.

With the incubation with the monospecific binder that specifically binds to a second binding specificity of the multispecific binder the multispecific binder is removed from the sample. Concomitantly also binding partner-multispecific binder-complexes are removed from the sample.

In one embodiment the multispecific binder is selected from antibody, a fusion polypeptide comprising an antibody or antibody fragment and non-antibody polypeptide, a fusion polypeptide comprising an antibody or antibody fragment and a soluble receptor, or a fusion polypeptide comprising an antibody or antibody fragment and a peptidic binding molecule.

In one embodiment the multispecific binder is an antibody. In one embodiment the antibody is a bispecific antibody, or a trispecific antibody, or a tetraspecific antibody, or a pentaspecific antibody, or a hexaspecific antibody. In one embodiment the antibody is a bispecific antibody.

In one embodiment the monospecific binder is an anti-idiotypic antibody.

In one embodiment the binding specificity is a binding site or a pair of an antibody heavy chain variable domain and an antibody light chain variable domain.

In one embodiment the anti-idiotypic antibody is bound to a solid phase.

In one embodiment the anti-idiotypic antibody is biotinylated and the solid phase is streptavidin coated. In one embodiment the solid phase is a streptavidin coated paramagnetic bead or a streptavidin coated sepharose bead.

One aspect as reported herein is a method for the immunological determination of the presence and/or amount of a binding partner of a multispecific binder in a sample using an immunoassay, wherein the multispecific binder is depleted from the sample prior to the determination of the binding partner.

In one embodiment of all aspects as reported herein is the binding partner the free binding partner, i.e. binding partner that is not bound or complexed by the multispecific binder.

In one embodiment the anti-idiotypic antibody is a biotinylated anti-idiotypic antibody against the multispecific binder and is conjugated to a solid phase via streptavidin.

In one embodiment of the methods as reported herein the anti-idiotypic antibody is a mixture comprising at least two anti-idiotypic antibodies that differ in the antibody site at which they are conjugated to the solid phase.

In one embodiment the conjugation of an antibody to its conjugation partner is performed by chemically binding via N-terminal and/or ε-amino groups (lysine), ε-amino groups of different lysins, carboxy-, sulfhydryl-, hydroxyl- and/or phenolic functional groups of the amino acid backbone of the drug antibody and/or sugar alcohol groups of the carbohydrate structure of the drug antibody.

In one embodiment the anti-idiotypic antibody mixture comprises the anti-idiotypic antibody conjugated via at least two different amino groups to the solid phase. Such coupling via different amino groups can be performed by acylation of a part of the ε-amino groups with chemical protecting agents, e.g. by citraconylation, in a first step. In a second step conjugation is performed via the remaining amino groups. Subsequently citraconylation is removed and the antibody is conjugated to the solid phase via remaining free amino groups, i.e. the antibody obtained is conjugated to the solid phase via amino groups that have not been protected by citraconylation. Suitable chemical protecting agents form bonds at unprotected side chain amines and are less stable than and different from those bonds at the N-terminus. Many such chemical protecting agents are known (see for example EP 0 651 761). In one embodiment the chemical protecting agents include cyclic dicarboxylic acid anhydrides like maleic or citraconylic acid anhydride.

In one embodiment the anti-idiotypic antibody is conjugated to the solid phase by passive adsorption. Passive adsorption is, e.g., described by Butler, J. E., in "Solid Phases in Immunoassay" (1996) 205-225 and Diamandis, E. P., and Christopoulos, T. K. (Editors), in "Immunoassays" (1996) Academic Press (San Diego).

In one embodiment the anti-idiotypic antibody is conjugated (immobilized) via a specific binding pair. Such a binding pair (first component/second component) is in one embodiment selected from streptavidin or avidin/biotin, antibody/antigen (see, for example, Hermanson, G. T., et al., Bioconjugate Techniques, Academic Press (1996), lectin/polysaccharide, steroid/steroid binding protein, hormone/hormone receptor, enzyme/substrate, IgG/Protein A and/or G, etc. In one embodiment the anti-idiotypic antibody is conjugated to biotin and immobilization is performed via immobilized avidin or streptavidin.

One aspect as reported herein is an in vitro method for the determination of the presence and/or amount of an antigen of a multispecific antibody in a sample, whereby the antigen to be detected can be specifically bound by a first binding specificity of the multispecific antibody, comprising the step of:

incubating a sample comprising the multispecific antibody, multispecific antibody bound antigen and free antigen with an anti-idiotypic antibody that specifically binds to a second binding specificity of the multispecific antibody, which is different from the first binding specificity.

In one embodiment the method comprises the steps of:
incubating a sample comprising antigen and multispecific antibody with an anti-idiotypic antibody that specifically binds to a second binding specificity of the multispecific antibody which is different from the first binding specificity, and
determining the amount of the antigen in the multispecific antibody-depleted sample.

In one embodiment the method comprises the step of:
incubating a sample comprising antigen and multispecific antibody with an anti-idiotypic antibody that specifically binds to a second binding specificity of the multispecific antibody which is different from the first binding specificity,
depleting the anti-idiotypic antibody-multispecific antibody-complex from the sample prior to the determination of the presence or the amount of free antigen, and
determining the amount of the antigen in the multispecific antibody-depleted sample.

With the incubation with the anti-idiotypic antibody that specifically binds to a second binding specificity of the multispecific antibody the multispecific antibody is removed from the sample. Concomitantly also antigen-multispecific antibody-complexes are removed from the sample.

In one embodiment the sample comprises multispecific antibody, free antigen and multispecific antibody-antigen complexes and the detection is of free antigen of the multispecific antibody.

In one embodiment the anti-idiotypic antibody is conjugated to a paramagnetic bead.

In one embodiment the anti-idiotypic antibody is conjugated to a solid phase.

In one embodiment the anti-idiotypic antibody is biotinylated and the solid phase is streptavidin coated. In one embodiment the solid phase is a streptavidin coated paramagnetic bead or a streptavidin coated sepharose bead.

In one embodiment the anti-idiotypic antibody has an association constant $k_a$ of $10^5$ l/mol*s or more to the second binding specificity of the multispecific antibody.

In one embodiment the anti-idiotypic antibody has a $K_D$ value of $5*10^{-8}$ mol/l or less for the binding to the second binding specificity of the multispecific antibody.

In one embodiment the binding specificity is a binding site. In one embodiment the binding site is a pair of an antibody heavy chain variable domain and an antibody light chain variable domain.

In one embodiment the incubating with the anti-idiotypic antibody is for about 10 minutes to about 36 hours.

In one embodiment the sample is adjusted to a multispecific antibody concentration of about 2 µg/ml to about 15 µg/ml.

In one embodiment the sample is adjusted to a total antigen concentration of from about 1 ng/ml to about 250 ng/ml.

In one embodiment the method comprises the following steps:
incubating a sample comprising the multispecific antibody, multispecific antibody-bound antigen and free antigen with an anti-idiotypic antibody that specifically binds to a second binding specificity of the multispecific antibody which is different from the first binding specificity, to form an anti-idiotypic antibody-multispecific antibody complex, and removing the anti-idiotypic antibody-multispecific antibody complex from the sample.

In one embodiment the anti-idiotypic antibody-multispecific antibody complex is a mixture of anti-idiotypic antibody-multispecific antibody complex and anti-idiotypic antibody-multispecific antibody-antigen complex.

In one embodiment the method comprises the following steps:

incubating a sample comprising antigen and multispecific antibody with an anti-idiotypic antibody that specifically binds to a second binding specificity of the multispecific antibody which is different from the first binding specificity, to form an anti-idiotypic antibody-multispecific antibody complex, removing the anti-idiotypic antibody-multispecific antibody complex from the sample, and determining the amount of the antigen in the multispecific-antibody depleted sample.

In one embodiment the determining of the amount of the antigen comprises the following steps:

incubating a multispecific antibody-depleted sample with a capture antibody that specifically binds to the antigen to form a capture antibody-antigen complex, and correlating the formed capture antibody-antigen complex to the amount of the antigen in the sample.

In one embodiment the determining of the amount of the antigen comprises the following steps:

incubating a multispecific antibody-depleted sample with a capture antibody that specifically binds to the antigen to form a capture antibody-antigen complex, incubating the capture antibody-antigen complex with a tracer antibody, whereby the capture antibody and the tracer antibody bind to non-overlapping epitope on the antigen, and correlating the formed capture antibody-antigen-tracer antibody complex to the amount of the antigen in the sample.

In one embodiment the determining of the amount of the antigen comprises the following steps:

incubating a multispecific antibody-depleted sample with a capture antibody that specifically binds to the antigen to form a capture antibody-antigen complex, incubating the capture antibody-antigen complex with a tracer antibody, whereby the capture antibody and the tracer antibody bind to non-overlapping epitope on the antigen, incubating the capture antibody-antigen-tracer antibody complex with a detection antibody comprising a detectable label, whereby the detection antibody specifically binds to the tracer antibody at an epitope outside the variable domains of the tracer antibody, and correlating the formed capture antibody-antigen-tracer antibody complex to the amount of the antigen in the sample.

In one embodiment the multispecific antibody is a bispecific antibody that has a first binding specificity that specifically binds to a first antigen or first epitope on an antigen and that has a second binding specificity that specifically binds to a second antigen or to a second epitope on the antigen.

One aspect as reported herein is the use of an anti-idiotypic antibody that specifically binds to a first binding specificity of a multispecific antibody for the depletion of antigen bound to the second binding specificity of the multispecific antibody from a sample.

DETAILED DESCRIPTION OF THE INVENTION

Herein is reported an in vitro method for the pre-treatment of a sample to detect "free binding partner" of multispecific binders, such as bispecific antibodies/drugs, in pre-clinical and clinical samples.

It has been found that the multispecific binder has to be depleted from the sample prior to the detection of the free binding partner.

Herein is reported the use of anti-idiotypic antibodies that specifically bind to a binding specificity of a therapeutic multispecific antibody in the determination of the level of antigen that can be but is not bound by a second different binding specificity of the multispecific therapeutic antibody. The anti-idiotypic antibody is used for the depletion of the multispecific antibody and multispecific antibody-antigen to be detected-complexes from a sample.

Thus, herein is reported an in vitro method for the determination of free binding partner (antigen, target, analyte) of a multispecific binder that can be specifically bound by a first binding specificity of the multispecific binder, wherein the multispecific binder is depleted from the sample prior to the determination of the free binding partner by incubating the sample with a monospecific binder that specifically binds to a second binding specificity of the multispecific binder that is different from the first binding specificity and therewith depletes the multispecific binder and multispecific binder-binding partner-complexes from the sample.

The determination of total antigen, bispecific antibody-bound antigen and free antigen is helpful for monitoring of therapies with therapeutic antibodies. Total antigen represents the sum of free and bispecific antibody-bound antigen, In the following the method as reported herein is exemplified with a multispecific antibody which specifically binds to a multitude of antigens or epitopes on the same antigen as embodiment of a multispecific binder and with an antigen which is specifically bound by one binding specificity of a multispecific antibody as embodiment of binding partner.

The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity.

In certain embodiments, the antibody is a multispecific antibody, e.g. a bispecific antibody. Multispecific antibodies are monoclonal antibodies that have binding specificities for at least two different sites. In certain embodiments, one of the binding specificities is for a first antigen and the other is for a different second antigen. In certain embodiments, bispecific antibodies may bind to two different epitopes of the same antigen. Bispecific antibodies can be prepared as full length antibodies or antibody fragments. In one embodiment the antibody is a bispecific antibody which specifically binds to a first and a second antigen. In one embodiment the bispecific antibody has i) a first binding specificity that specifically binds to a first antigen or a first epitope on an antigen, and ii) a second binding specificity that specifically binds to a second antigen or a second epitope on the same antigen. In one embodiment the second epitope on the same antigen is a non-overlapping epitope.

Multispecific antibodies are described in WO 2009/080251, WO 2009/080252, WO 2009/080253, WO 2009/080254, WO 2010/112193, WO 2010/115589, WO 2010/136172, WO 2010/145792, or WO 2010/145793.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')$_2$; diabodies; linear antibodies; single-chain antibody molecules (e.g. scFv); and multispecific antibodies formed from antibody fragments.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., IgG$_1$, IgG$_2$, IgG$_3$, IgG$_4$, IgA$_1$, and IgA$_2$. The heavy chain constant domains that correspond to the different classes of immunoglobulins are called α, δ, ε, γ, and μ, respectively.

The term "free antigen" denotes the antigen that can be specifically bound by a binding specificity of an antibody but which is currently not bound to this binding specificity. In one embodiment the free antigen is a not-antibody bound antigen or a non-antibody complexed antigen.

The term "Fc-region" herein is used to define a C-terminal region of an immunoglobulin heavy chain that contains at least a portion of the constant region.

The term includes native sequence Fc-regions and variant Fc-regions. In one embodiment, a human IgG heavy chain Fc-region extends from Cys226, or from Pro230, to the carboxyl-terminus of the heavy chain. However, the C-terminal lysine (Lys447) of the Fc-region may or may not be present. Unless otherwise specified herein, numbering of amino acid residues in the Fc-region or constant region is according to the EU numbering system, also called the EU index, as described in Kabat, E. A. et al., Sequences of Proteins of Immunological Interest, 5th ed., Public Health Service, National Institutes of Health, Bethesda, Md. (1991), NIH Publication 91-3242.

"Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3 (L3)-FR4.

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

The term "hypervariable region" or "HVR", as used herein, refers to each of the regions of an antibody variable domain which are hypervariable in sequence and/or form structurally defined loops ("hypervariable loops"). Generally, native four-chain antibodies comprise six HVRs; three in the VH (H1, H2, H3), and three in the VL (L1, L2, L3). HVRs generally comprise amino acid residues from the hypervariable loops and/or from the "complementarity determining regions" (CDRs), the latter being of highest sequence variability and/or involved in antigen recognition. Exemplary hypervariable loops occur at amino acid residues 26-32 (L1), 50-52 (L2), 91-96 (L3), 26-32 (H1), 53-55 (H2), and 96-101 (H3) (Chothia, C. and Lesk, A. M., J. Mol. Biol. 196 (1987) 901-917). Exemplary CDRs (CDR-L1, CDR-L2, CDR-L3, CDR-H1, CDR-H2, and CDR-H3) occur at amino acid residues 24-34 of L1, 50-56 of L2, 89-97 of L3, 31-35B of H1, 50-65 of H2, and 95-102 of H3 (Kabat, E. A. et al., Sequences of Proteins of Immunological Interest, 5th ed. Public Health Service, National Institutes of Health, Bethesda, Md. (1991), NIH Publication 91-3242). With the exception of CDR1 in VH, CDRs generally comprise the amino acid residues that form the hypervariable loops. CDRs also comprise "specificity determining residues," or "SDRs," which are residues that contact antigen. SDRs are contained within regions of the CDRs called abbreviated-CDRs, or a-CDRs. Exemplary a-CDRs (a-CDR-L1, a-CDR-L2, a-CDR-L3, a-CDR-H1, a-CDR-H2, and a-CDR-H3) occur at amino acid residues 31-34 of L1, 50-55 of L2, 89-96 of L3, 31-35B of H1, 50-58 of H2, and 95-102 of H3 (Almagro, J. C. and Fransson, J., Front. Biosci. 13 (2008) 1619-1633). Unless otherwise indicated, HVR residues and other residues in the variable domain (e.g., FR residues) are numbered herein according to Kabat et al., supra.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs) (see, e.g., Kindt, T. J. et al. Kuby Immunology, 6th ed., W.H. Freeman and Co., N.Y. (2007), page 91). A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively (see, e.g., Portolano, S. et al., J. Immunol. 150 (1993) 880-887; Clackson, T. et al., Nature 352 (1991) 624-628).

The term "anti-idiotypic antibody" denotes an antibody, which specifically binds to a binding specificity such as a binding site of a parent antibody, i.e. which is directed e.g. against an antigen binding site of a parent antibody. In one embodiment the anti-idiotypic antibody specifically binds to one or more of the CDRs of the parent antibody. In one embodiment the parent antibody is a therapeutic antibody. In one embodiment the parent antibody is a multispecific antibody. In one embodiment the parent antibody is a bispecific antibody.

Two epitopes are overlapping if a signal reduction of 50% or more, in one embodiment of 75% or more, is detected by a surface plasmon resonance (SPR) assay using the immobilized antibody and soluble antigen, or vice versa, with the epitope in question at a concentration of 20-50 nM and the antibody for which the epitope overlap has to be detected at a concentration of 100 nM. Alternatively a method can be used in which epitope overlap of two antibodies binding to the same antigen is determined with the help of a competitive test system. For this purpose, for example with the help of a cell-based enzyme immunoassay (ELISA) employing cells expressing recombinant antigen epitopes, it is tested if the antibody for which the epitope overlap has to be detected competes with the other antibody for the binding to the immobilized antigen. For this purpose, the immobilized antigen is incubated with the antibody in labeled form and an excess of the antibody for which the epitope overlap has to be determined. By detection of the bound labeling there can easily be ascertained the epitope overlap. If a signal reduction of more than 70%, in one embodiment of more than 80%, at the same concentration, or a displacement of more than 80%, in one embodiment of more than 90%, at higher concentrations, in one case with a $10^5$-fold excess of the antibody for which epitope overlap has to be determined, referred to the known antibody is determined then epitope identity or overlap is present and both antibodies bind to the same or an overlapping epitope on the same antigen.

The principles of different immunoassays are described, for example, by Hage, D. S. (Anal. Chem. 71 (1999) 294R-304R). Lu, B., et al. (Analyst 121 (1996) 29R-32R) report the orientated immobilization of antibodies for the use in immunoassays. Avidin-biotin-mediated immunoassays are reported, for example, by Wilchek, M., and Bayer, E. A., in Methods Enzymol. 184 (1990) 467-469.

Monoclonal antibodies and their constant domains contain as proteins a number of reactive side chains for coupling to a binding partner, such as a surface, a protein, a polymer (e.g. PEG, cellulose or polystyrol), an enzyme, or a member of a binding pair. Chemical reactive groups of antibodies are, for example, amino groups (lysins, alpha-amino groups), thiol groups (cystins, cysteines, and methionins), carboxylic acid groups (aspartic acids, glutamic acids), and sugar-alcoholic groups. Such methods are e.g. described by Aslam M., and Dent, A., in "Bioconjugation", MacMillan Ref. Ltd. 1999, pp. 50-100.

One of the most common reactive groups of proteins is the aliphatic $\epsilon$-amine of the amino acid lysine. In general, nearly all antibodies contain abundant lysine. Lysine amines are reasonably good nucleophiles above pH 8.0 ($pK_a$=9.18) and therefore react easily and cleanly with a variety of reagents to form stable bonds. Amine-reactive reagents react primarily with lysins and the $\alpha$-amino groups of proteins. Reactive esters, particularly N-hydroxy-succinimide (NHS) esters, are among the most commonly employed reagents for modification of amine groups. The optimum pH for reaction in an aqueous environment is pH 8.0 to 9.0. Isothiocyanates are amine-modification reagents and form thiourea bonds with proteins. They react with protein amines in aqueous solution (optimally at pH 9.0 to 9.5). Aldehydes react under mild aqueous conditions with aliphatic and aromatic amines, hydrazines, and hydrazides to form an imine intermediate (Schiff's base). A Schiff's base can be selectively reduced with mild or strong reducing agents (such as sodium borohydride or sodium cyanoborohydride) to derive a stable alkyl amine bond. Other reagents that have been used to modify amines are acid anhydrides. For example, diethylenetriaminepentaacetic anhydride (DTPA) is a bifunctional chelating agent that contains two amine-reactive anhydride groups. It can react with N-terminal and $\epsilon$-amine groups of proteins to form amide linkages.

The anhydride rings open to create multivalent, metal-chelating arms able to bind tightly to metals in a coordination complex.

Another common reactive group in antibodies is the thiol residue from the sulfur-containing amino acid cystine and its reduction product cysteine (or half cystine). Cysteine contains a free thiol group, which is more nucleophilic than amines and is generally the most reactive functional group in a protein. Thiols are generally reactive at neutral pH, and therefore can be coupled to other molecules selectively in the presence of amines. Since free sulfhydryl groups are relatively reactive, proteins with these groups often exist with them in their oxidized form as disulfide groups or disulfide bonds. In such proteins, reduction of the disulfide bonds with a reagent such as dithiothreitol (DTT) is required to generate the reactive free thiol. Thiol-reactive reagents are those that will couple to thiol groups on proteins, forming thioether-coupled products. These reagents react rapidly at slight acidic to neutral pH and therefore can be reacted selectively in the presence of amine groups. The literature reports the use of several thiolating crosslinking reagents such as Traut's reagent (2-iminothiolane), succinimidyl (acetylthio) acetate (SATA), and sulfosuccinimidyl 6-[3-(2-pyridyldithio) propionamido]hexanoate (Sulfo-LC-SPDP) to provide efficient ways of introducing multiple sulfhydryl groups via reactive amino groups. Haloacetyl derivatives, e.g. iodoacetamides, form thioether bonds and are also reagents for thiol modification. Further useful reagents are maleimides. The reaction of maleimides with thiol-reactive reagents is essentially the same as with iodoacetamides. Maleimides react rapidly at slight acidic to neutral pH.

Another common reactive group in antibodies are carboxylic acids. Proteins contain carboxylic acid groups at the C-terminal position and within the side chains of aspartic acid and glutamic acid. The relatively low reactivity of carboxylic acids in water usually makes it difficult to use these groups to selectively modify proteins and other biomolecules. When this is done, the carboxylic acid group is usually converted to a reactive ester by the use of a water-soluble carbodiimide and reacted with a nucleophilic reagent such as an amine, hydrazide, or hydrazine. The amine-containing reagent should be weakly basic in order to react selectively with the activated carboxylic acid in the presence of the more highly basic $\epsilon$-amines of lysine to form a stable amide bond. Protein crosslinking can occur when the pH is raised above 8.0.

Sodium periodate can be used to oxidize the alcohol part of a sugar within a carbohydrate moiety attached to an antibody to an aldehyde. Each aldehyde group can be reacted with an amine, hydrazide, or hydrazine as described for carboxylic acids. Since the carbohydrate moiety is predominantly found on the crystallizable fragment (Fc) region of an antibody, conjugation can be achieved through site-directed modification of the carbohydrate away from the antigen-binding site. A Schiff's base intermediate is formed, which can be reduced to an alkyl amine through the reduction of the intermediate with sodium cyanoborohydride (mild and selective) or sodium borohydride (strong) water-soluble reducing agents.

The term "sample" includes, but is not limited to, any quantity of a substance from a living thing or formerly living thing. Such living things include, but are not limited to, humans, mice, monkeys, rats, rabbits, and other animals. In one embedment the sample is obtained from a monkey, especially a cynomolgus monkey, or a rabbit, or a mouse or rat. Such substances include, but are not limited to, in one embodiment whole blood, serum, or plasma from an individual, which are the most widely used sources of sample in clinical routine.

The term "solid phase" denotes a non-fluid substance, and includes particles (including microparticles and beads) made from materials such as polymer, metal (paramagnetic, ferromagnetic particles), glass, and ceramic; gel substances such as silica, alumina, and polymer gels; capillaries, which may be made of polymer, metal, glass, and/or ceramic; zeolites and other porous substances; electrodes; microtiter plates; solid strips; and cuvettes, tubes or other spectrometer sample containers. A solid phase component is distinguished from inert solid surfaces in that a "solid phase" contains at least one moiety on its surface, which is intended to interact with a substance in a sample. A solid phase may be a stationary component, such as a tube, strip, cuvette or microtiter plate, or may be non-stationary components, such as beads and microparticles. A variety of microparticles that allow either non-covalent or covalent attachment of proteins and other substances may be used. Such particles include polymer particles such as polystyrene and poly(methylmethacrylate); gold particles such as gold nanoparticles and gold colloids; and ceramic particles such as silica, glass, and metal oxide particles. See for example Martin, C. R., et al., Analytical Chemistry-News & Features, 70 (1998) 322A-327A, or Butler, J. E., Methods 22 (2000) 4-23.

From chromogens (fluorescent or luminescent groups and dyes), enzymes, NMR-active groups, metal particles, or haptens, such as digoxygenin, the detectable label is selected in one embodiment. The detectable label can also be a photoactivatable crosslinking group, e.g. an azido or an azirine group. Metal chelates which can be detected by electrochemiluminescence are also in one embodiment signal-emitting groups, with particular preference being given to ruthenium chelates, e.g. a ruthenium (bispyridyl)$_3^{2+}$ chelate. Suitable ruthenium labeling groups are described, for example, in EP 0 580 979, WO 90/05301, WO 90/11511, and WO 92/14138.

Herein is reported a method for the determination of the presence and/or the amount of (free) antigen of a multispecific antibody in a sample comprising a solid phase immobilized anti-idiotypic antibody that specifically binds to one binding specificity of the multispecific antibody that is not the binding specificity of the multispecific antibody that specifically binds to the (free) antigen to be determined for the depletion of the multispecific antibody, either in complexed form or in non-complexed form, from the sample prior to the determination of the amount of the (free) antigen.

In one embodiment the determination of the presence and/or amount of the antigen in the multispecific antibody-depleted sample is by an antigen bridging immunoassay. In one embodiment the immunoassay comprises a capture antibody and a tracer antibody, wherein the capture is conjugated to a solid phase, and the tracer antibody is conjugated to a detectable label.

In one embodiment the method comprises the depletion the monospecific binder-multispecific binder-complex from the sample prior to the determination of the presence or the amount of free binding partner.

One aspect as reported herein is an in vitro method for the determination of the presence and/or the amount of an antigen of a multispecific antibody in a sample, whereby the antigen to be detected can be specifically bound by a first binding specificity of the multispecific antibody, comprising the step of:
  incubating a sample comprising the antigen and the multispecific antibody with an anti-idiotypic antibody that specifically binds to a second binding specificity of the multispecific antibody which is different from the first binding specificity, and thereby removing the multispecific antibody from the sample.

A person skilled in the art knows that a sample that comprises an antigen and an antibody that can specifically bind the antigen comprises a mixture of free antigen, antibody-bound antigen and free antibody due to equilibrium thermodynamics.

In one embodiment the method comprises the following steps:
  incubating a sample comprising the antigen and the multispecific antibody with an anti-idiotypic antibody that specifically binds to a second binding specificity of the multispecific antibody which is different from the first binding specificity, to form an anti-idiotypic antibody-multispecific antibody complex, and
  removing the anti-idiotypic antibody-multispecific antibody complex from the sample.

In one embodiment the method comprises the following steps:
  incubating a sample comprising the antigen and the multispecific antibody with an anti-idiotypic antibody that specifically binds to a second binding specificity of the multispecific antibody which is different from the first binding specificity, to form an anti-idiotypic antibody-multispecific antibody complex,
  removing the anti-idiotypic antibody-multispecific antibody complex from the sample, and
  determining the amount of the antigen in the multispecific-antibody depleted sample.

In one embodiment the method comprises the step of:
  depleting the monospecific binder-multispecific binder-complex from the sample prior to the determination of the presence or the amount of free binding partner.

In one embodiment the method comprises the step of:
  incubating a sample comprising binding partner and multispecific binder with an monospecific binder that specifically binds to a second binding specificity of the multispecific binder which is different from the first binding specificity,
  depleting the monospecific binder-multispecific binder-complex from the sample prior to the determination of the presence or the amount of free binding partner, and
  determining the amount of the binding partner in the multispecific binder-depleted sample.

In one embodiment the determining the presence and/or the amount of the antigen is by an antigen bridging immunoassay.

In one embodiment the determining of the presence and/or the amount of the antigen is the determining of the amount of the free antigen.

In one embodiment the determining of the presence and/or amount of the antigen comprises the following steps:
incubating a multispecific antibody-depleted sample with a capture antibody that specifically binds to the antigen to form a capture antibody-antigen complex, and
correlating the amount of formed capture antibody-antigen complex to the amount of the antigen in the sample.

In one embodiment the determining of the presence and/or amount of the antigen comprises the following steps:
incubating a multispecific antibody-depleted sample with a capture antibody specifically binding to the antigen to form a capture antibody-antigen complex,
incubating the capture antibody-antigen complex with a tracer antibody, whereby the capture antibody and the tracer antibody bind to non-overlapping epitope on the antigen, and
correlating the formed capture antibody-antigen-tracer antibody complex to the amount of the antigen in the sample.

In one embodiment the tracer antibody comprises a detectable label.

In one embodiment the determining of the presence and/or amount of the antigen comprises the following steps:
incubating a multispecific antibody-depleted sample with a capture antibody that specifically binds to the antigen to form a capture antibody-antigen complex,
incubating the capture antibody-antigen complex with a tracer antibody, whereby the capture antibody and the tracer antibody bind to non-overlapping epitope on the antigen,
incubating the capture antibody-antigen-tracer antibody complex with a detection antibody comprising a detectable label, whereby the detection antibody specifically binds to the tracer antibody at an epitope outside the variable domains of the tracer antibody, and
correlating the formed capture antibody-free antigen-tracer antibody complex to the amount of the antigen in the sample.

In one embodiment the capture antibody and the tracer antibody bind to non-overlapping epitope on the antigen.

In one embodiment the anti-idiotypic antibody and/or the capture antibody are conjugated to a solid phase.

The anti-idiotypic antibody and/or the capture antibody useful in a method as reported herein can be conjugated to a solid phase. The conjugation is in one embodiment performed by chemical binding via N-terminal and/or $\epsilon$-amino groups (lysine), $\epsilon$-amino groups of different lysins, carboxy-, sulfhydryl-, hydroxyl- and/or phenolic functional groups of the amino acid backbone of the antibody and/or sugar alcohol groups of the carbohydrate structure of the antibody. The anti-idiotypic antibody and/or the capture antibody is in one embodiment a mixture of at least two antibodies conjugated to a solid phase, wherein the at least two antibodies conjugated to a solid phase differ in the site at which they are conjugated to the solid phase. For example, the mixture of at least two antibodies conjugated to a solid phase may comprise an antibody conjugated via an amino acid of the amino acid backbone of the antibody to the solid phase and an antibody conjugated via a sugar alcohol group of a carbohydrate structure of the antibody to the solid phase. Also, for example, the mixture of at least two antibodies conjugated to a solid phase may comprise antibodies conjugated to the solid phase via different amino acid residues of their amino acid backbone. The expression "different amino acid residue" denotes either two different kinds of amino acids, such as e.g. lysine and aspartic acid, or tyrosine and glutamic acid, or two amino acid residues of the amino acid backbone differing in their position in the amino acid sequence of the antibody. In the latter case the amino acid can be of the same kind or of different kind. The expression "differ in the antibody site" denotes a difference either in the kind of site, e.g. amino acid or sugar alcohol group, or in the number of the amino acid of the amino acid backbone, e.g. at which the antibody is conjugated to the solid phase. The same applies vice versa to the tracer antibody useful in a method as reported herein.

In one embodiment of the method the immunoassay comprises a capture antibody, a tracer antibody and a detection antibody, wherein the capture antibody is a biotinylated antibody against the antigen conjugated to a solid phase via streptavidin, the tracer antibody is an antibody against the antigen conjugated to digoxygenin, and the detection antibody is an antibody against digoxygenin conjugated to horseradish peroxidase.

The general method for depletion of complexes consisting of bispecific antibodies which specifically bind to antigen X and antigen Y and from samples comprising antigen X and/or antigen Y for the determination of antigen X or antigen Y, respectively, comprises the following steps:
assembly of complexes between bispecific antibody which specifically binds to antigen X and antigen Y (anti-X/Y antibody):
A constant concentration of antigen X is incubated with increasing amount of the bispecific monoclonal antibody, which specifically binds to antigen X with a first binding specificity and which specifically binds to antigen Y with a second binding specificity (anti-X/Y antibody), at room temperature for 1 hour. Afterwards, this sample is used as positive control in the depletion step.
depletion step:
For depletion of antigen X bound to an anti-X/Y antibody a biotinylated anti-idiotypic antibody against the binding specificity which specifically binds to antigen Y (anti-id Y antibody-BI) is bound to magnetic streptavidin coated beads (SA-beads) at about 10 μg/ml. For each sample, 600 μl SA-Beads are washed and separated from supernatant with a magnetic separator. 600 μl of a biotinylated anti-id Y antibody containing solution is mixed with the SA-Beads and incubated for about one hour at room temperature. The excess of unbound anti-idiotypic antibody was removed by 3-times washing of the beads with a magnetic separator. Afterwards, the anti-idiotypic antibody coated beads were incubated with about 250 μl of a sample containing complexes of anti-X/Y antibody and antigen X. The mixture is incubated at room temperature with shaking for about one hour. After incubation, the beads are separated from the sample with a magnetic separator. The supernatant is taken for analysis of "free" antigen X in ELISA (see e.g. Example 2). The remaining beads were transferred into ELECSYS container and bead-bound antigen X (bispecific antibody-bound antigen X) is analyzed with ELECSYS 2010 analyzer according standard operational procedures of the user guide (see e.g. Example 3).

For depletion of antigen Y bound to an anti-X/Y antibody a biotinylated anti-idiotypic antibody against the binding specificity which specifically binds to antigen X (anti-id X antibody-BI) is bound to magnetic streptavidin coated beads (SA-beads) at about 10 μg/ml. For each sample, 600 μl SA-Beads are washed and separated from supernatant with a magnetic separator. 600 μl of a biotinylated anti-id X antibody containing solution is mixed with the SA-Beads and incubated for about one hour at room temperature. The excess of unbound anti-idiotypic antibody was removed by 3-times washing of the beads with a magnetic separator. Afterwards, the anti-idiotypic antibody coated beads were incubated with about 250 μl of a sample containing complexes of anti-X/Y antibody and antigen Y. The mixture is incubated at room temperature with shaking for about one hour. After incubation, the beads are separated from the sample with a magnetic separator. The supernatant is taken for analysis of "free" antigen Y in ELISA (see e.g. Example 2). The remaining beads were transferred into ELECSYS container and bead-bound antigen Y (bispecific antibody-bound antigen Y) is analyzed with ELECSYS 2010 analyzer according standard operational procedures of the user guide (see e.g. Example 3).

In one embodiment the anti-idiotypic antibody has an association constant $k_a$ of $10^5$ l/mol*s or more. In one embodiment the anti-idiotypic antibody has an association constant of $1*10^5$ l/mol*s or more. In one embodiment the anti-idiotypic antibody further has a $K_D$ value of $5*10^{-8}$ mol/l or less. In one embodiment the anti-idiotypic antibody further has a $K_D$ value of $1*10^{-9}$ mol/l or less.

In one embodiment the incubating in the depletion step is for about 5 minutes to about 36 hours. In one embodiment the incubating in the depletion step is for about 15 minutes to about 30 hours.

In one embodiment the sample is adjusted to a multispecific antibody concentration of about 2 μg/ml to about 15 μg/ml. In one embodiment the sample is adjusted to a multispecific antibody concentration of about 3 μg/ml to about 12 μg/ml.

In one embodiment the sample is adjusted to a total antigen concentration of from about 1 pg/ml to about 1 μg/ml. In one embodiment the sample is adjusted to a total antigen concentration of from about 10 pg/ml to about 500 ng/ml. In one embodiment the sample is adjusted to a total antigen concentration of from about 100 pg/ml to about 250 ng/ml. In one embodiment the sample is adjusted to a total antigen concentration of about 1 ng/ml to about 100 ng/ml.

In case of a bispecific antibody against ANG2 and VEGF the mechanism of action is blockade of both antigens for binding on their corresponding receptors. In absence of free antigen (able to bind to the receptor), the signal pathway is inhibited. A differentiation between free antigen(s) and antibody-bound antigen(s) is advantageous.

The following examples and figures are provided to aid the understanding of the present invention, the true scope of which is set forth in the appended claims. It is understood that modifications can be made in the procedures set forth without departing from the spirit of the invention.

Specific Embodiments

1. A method for the in vitro determination of the presence and/or the amount of a binding partner, which can be specifically bound by a first binding specificity of a multispecific binder, wherein binding partner bound to the multispecific binder is depleted prior to the detection of the binding partner by incubating the sample with a monospecific binder specifically binding to a second binding specificity of the multispecific binder.

2. A method for the immunological determination of the presence and/or amount of a binding partner of a multispecific binder in a sample using an immunoassay, wherein the multispecific binder is depleted from the sample prior to the determination of the binding partner.

3. An in vitro method for the determination of the presence and/or the amount of a binding partner of a multispecific binder, whereby the binding partner can be specifically bound by a first binding specificity of the multispecific binder, comprising the step of:
   incubating a sample comprising binding partner and multispecific binder with a monospecific binder that specifically binds to a second binding specificity of the multispecific binder which is different from the first binding specificity.

4. An in vitro method for the determination of the presence and/or amount of an antigen of a multispecific antibody in a sample, whereby the antigen to be detected can be specifically bound by a first binding specificity of the multispecific antibody, comprising the step of:
   incubating a sample comprising the multispecific antibody, multispecific antibody bound antigen and free antigen with an anti-idiotypic antibody that specifically binds to a second binding specificity of the multispecific antibody, which is different from the first binding specificity.

5. The method according to any one of items 3 to 4, characterized in further comprising as second step the step of:
   depleting the monospecific binder-multispecific binder-complex from the sample prior to the determination of the presence and/or the amount of free binding partner.

6. The method according to any one of items 3 to 5, characterized in comprising as final step:
   determining the amount of the binding partner in the multispecific binder-depleted sample.

7. The method according to any one of items 2 to 6, characterized in comprising the following steps:
   incubating a sample comprising binding partner and multispecific binder with a monospecific binder that specifically binds to a second binding specificity of the multispecific binder which is different from the first binding specificity,
   depleting the monospecific binder-multispecific binder-complex from the sample prior to the determination of the presence or the amount of free binding partner, and
   determining the amount of the binding partner in the multispecific binder-depleted sample.

8. The method according to any one of items 1 to 7, characterized in that the binding partner is selected from the group comprising antigen, target, and analyte.

9. The method according to any one of items 1 to 8, characterized in that the binding partner is the non-complexed binding partner or the free binding partner.

10. The method according to any one of items 1 to 9, characterized in that the binding specificity is a binding site or a pair of an antibody heavy chain variable domain and an antibody light chain variable domain.

11. The method according to any one of items 1 to 10, characterized in that the multispecific binder is selected from antibody, a fusion polypeptide comprising an antibody or antibody fragment and non-antibody polypeptide, a fusion polypeptide comprising an antibody or antibody fragment and a soluble receptor, or a fusion polypeptide comprising an antibody or antibody fragment and a peptidic binding molecule.

12. The method according to any one of items 1 to 11, characterized in that the multispecific binder is an antibody.

13. The method according to any one of items 8 to 12, characterized in that the determining the presence and/or the amount of the antigen comprises the following steps:
incubating a multispecific antibody-depleted sample with a capture antibody that specifically binds to the antigen to form a capture antibody-antigen complex, and
correlating the formed capture antibody-antigen complex to the amount of the antigen in the sample.

14. The method according to any one of items 8 to 13, characterized in that the determining of the amount of the antigen comprises the following steps:
incubating a multispecific antibody-depleted sample with a capture antibody that specifically binds to the antigen to form a capture antibody-antigen complex,
incubating the capture antibody-antigen complex with a tracer antibody, whereby the capture antibody and the tracer antibody bind to non-overlapping epitope on the antigen, and
correlating the formed capture antibody-antigen-tracer antibody complex to the amount of the antigen in the sample.

15. The method according to any one of items 8 to 14, characterized in that the determining of the amount of the antigen comprises the following steps:
incubating a multispecific antibody-depleted sample with a capture antibody that specifically binds to the antigen to form a capture antibody-antigen complex,
incubating the capture antibody-antigen complex with a tracer antibody, whereby the capture antibody and the tracer antibody bind to non-overlapping epitope on the antigen,
incubating the capture antibody-antigen-tracer antibody complex with a detection antibody comprising a detectable label, whereby the detection antibody specifically binds to the tracer antibody at an epitope outside the variable domains of the tracer antibody, and
correlating the formed capture antibody-antigen-tracer antibody complex to the amount of the antigen in the sample.

16. The method according to any one of items 11 to 15, characterized in that the antibody is a bispecific antibody, or a trispecific antibody, or a tetraspecific antibody, or a pentaspecific antibody, or a hexaspecific antibody.

17. The method according to any one of items 11 to 16, characterized in that the antibody is a bispecific antibody.

18. The method according to any one of items 11 to 17, characterized in that the antibody is a bispecific antibody that has a first binding specificity that specifically binds to a first antigen or first epitope on an antigen and that has a second binding specificity that specifically binds to a second antigen or to a second epitope on the antigen.

19. The method according to any one of items 1 to 18, characterized in that the monospecific binder is an anti-idiotypic antibody.

20. The method according to item 19, characterized in that the method comprises the following steps:
incubating a sample comprising the multispecific antibody, multispecific antibody-bound antigen and free antigen with an anti-idiotypic antibody that specifically binds to a second binding specificity of the multispecific antibody which is different from the first binding specificity, to form an anti-idiotypic antibody-multispecific antibody complex, and
removing the anti-idiotypic antibody-multispecific antibody complex from the sample.

21. The method according to any one of items 19 to 20, characterized in that the method comprises the following steps:
incubating a sample comprising antigen and multispecific antibody with an anti-idiotypic antibody that specifically binds to a second binding specificity of the multispecific antibody which is different from the first binding specificity, to form an anti-idiotypic antibody-multispecific antibody complex,
removing the anti-idiotypic antibody-multispecific antibody complex from the sample, and
determining the amount of the antigen in the multispecific-antibody depleted sample.

22. The method according to any one of items 20 to 21, characterized in that the anti-idiotypic antibody-multispecific antibody complex is a mixture of anti-idiotypic antibody-multispecific antibody complex and anti-idiotypic antibody-multispecific antibody-antigen complex.

23. The method according to any one of items 19 to 22, characterized in that the anti-idiotypic antibody has an association constant $k_a$ of $10^5$ l/mol*s or more to the second binding specificity of the multispecific antibody.

24. The method according to any one of items 19 to 23, characterized in that the anti-idiotypic antibody has a $K_D$ value of $5*10^{-8}$ mol/l or less for the binding to the second binding specificity of the multispecific antibody.

25. The method according to any one of items 19 to 24, characterized in that the incubating with the anti-idiotypic antibody is for about 10 minutes to about 36 hours.

26. The method according to any one of items 1 to 25, characterized in that the sample is adjusted to a multispecific antibody concentration of about 2 µg/ml to about 15 µg/ml.

27. The method according to any one of items 1 to 26, characterized in that the sample is adjusted to a total antigen concentration of from about 1 ng/ml to about 250 ng/ml.

28. The method according to any one of items 19 to 27, characterized in that the anti-idiotypic antibody is bound or conjugated to a solid phase.

29. The method according to any one of items 19 to 28, characterized in that the anti-idiotypic antibody is conjugated (immobilized) via a specific binding pair.

30. The method according to item 29, characterized in that the binding pair (first component/second component) is selected from streptavidin or avidin/biotin, antibody/antigen, lectin/polysaccharide, steroid/steroid binding protein, hormone/hormone receptor, enzyme/substrate, IgG/Protein A and/or G.

31. The method according to any one of items 29 to 30, characterized in that the anti-idiotypic antibody is conjugated to biotin and immobilization is performed via immobilized avidin or streptavidin.

32. The method according to any one of items 19 to 31, characterized in that the anti-idiotypic antibody is biotinylated and the solid phase is streptavidin coated.

33. The method according to any one of items 19 to 31, characterized in that the anti-idiotypic antibody is a biotinylated anti-idiotypic antibody against the multispecific binder and is conjugated to a solid phase via streptavidin.

34. The method according to any one of items 28 to 33, characterized in that the solid phase is a streptavidin coated paramagnetic bead or a streptavidin coated sepharose bead.
35. The method according to any one of items 19 to 34, characterized in that the anti-idiotypic antibody is a mixture comprising at least two anti-idiotypic antibodies that differ in the antibody site at which they are conjugated to the solid phase.
36. The method according to any one of items 19 to 35, characterized in that the anti-idiotypic antibody mixture comprises the anti-idiotypic antibody conjugated via at least two different amino groups to the solid phase.
37. The method according to any one of items 28 to 36, characterized in that the conjugation of the anti-idiotypic antibody to its conjugation partner is performed by chemically binding via N-terminal and/or ε-amino groups (lysine), and/or ε-amino groups of different lysins, carboxy-, sulfhydryl-, hydroxyl- and/or phenolic functional groups of the amino acid backbone of the drug antibody, and/or sugar alcohol groups of the carbohydrate structure of the drug antibody.
38. The method according to any one of items 28 to 37, characterized in that the anti-idiotypic antibody is conjugated to the solid phase by passive adsorption.
39. The method according to any one of items 1 to 38, characterized in that the sample comprises multispecific antibody, free antigen and multispecific antibody-antigen complexes and the detection is of free antigen of the multispecific antibody.
40. The use of an anti-idiotypic antibody that specifically binds to a first binding specificity of a multispecific antibody for the depletion of antigen bound to the second binding specificity of the multispecific antibody from a sample.

EXAMPLES

Example 1

Figure 1:
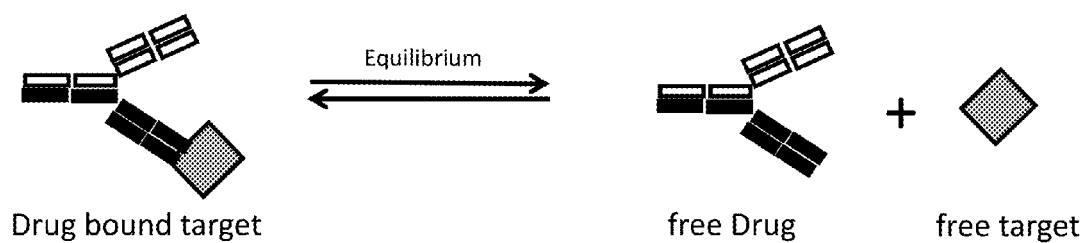
FIG. 1 Equilibrium between drug-bound target (antigen bound to bispecific antibody) and free target (free antigen).
Figure 2:
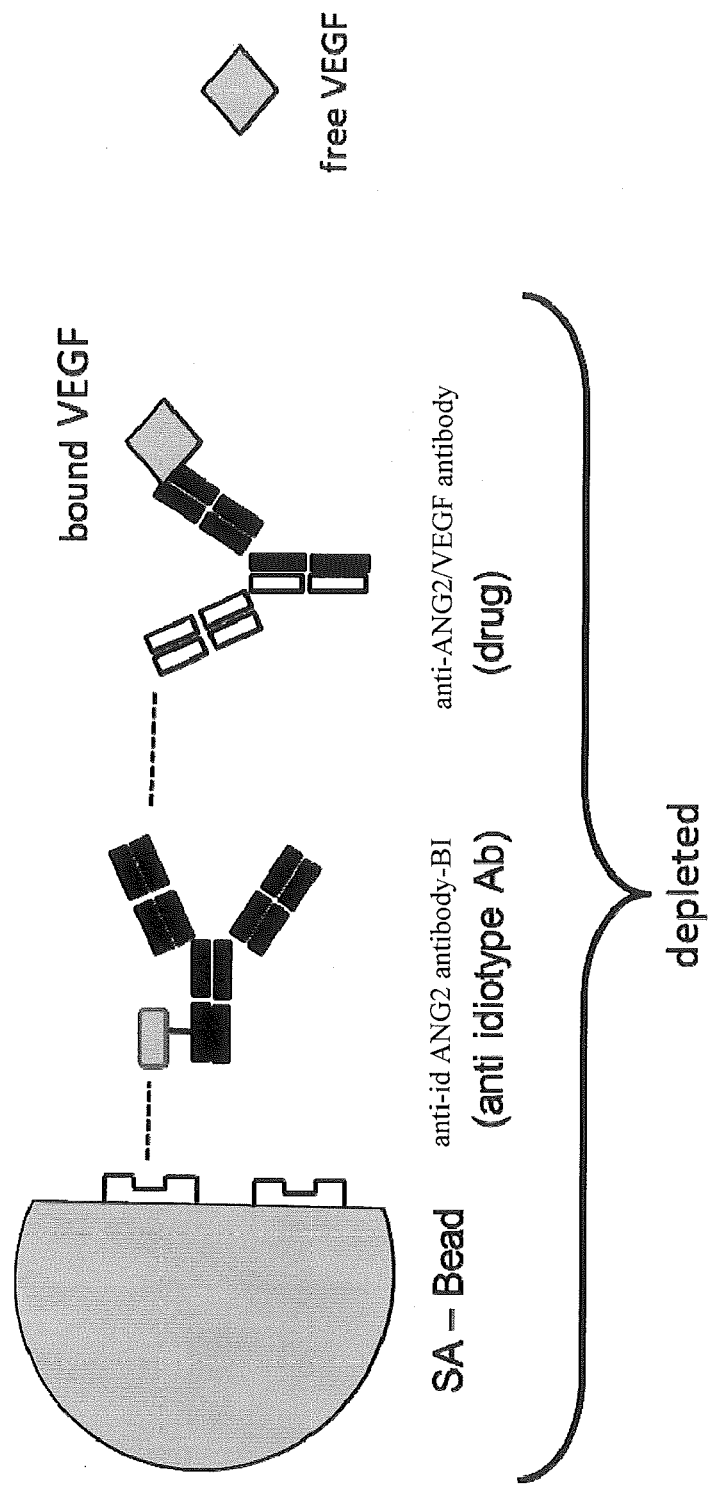
FIG. 2 Depletion of VEGF bound to a bispecific anti-ANG2/VEGF antibody by use of an anti-idiotypic antibody directed to the ANG2 binding specificity of the bispecific antibody; a biotinylated anti-idiotypic antibody against the ANG2 binding specificity of the bispecific antibody is immobilized on streptavidin-coated magnet-beads; after incubation of these magnet beads with a sample, e.g. serum sample, bispecific anti-ANG2/VEGF antibody is bound and depleted by immobilized anti-idiotypic antibody; VEGF bound to the bispecific antibody is co-depleted; free VEGF (not-bound to the bispecific antibody) remains in the supernatant of the serum sample.

Depletion of Drug-Bound Target (Antibody-Bound Antigen)—in Cases of Bispecific Drug Molecules Depletion of Anti-ANG2/VEGF Antibody-VEGF Complexes from a Sample
A) Assembly of Complexes of Anti-ANG2/VEGF Antibody and VEGF A constant concentration of VEGF was incubated with an increasing amount of bispecific antibody which specifically binds to ANG2 with a first binding specificity and which specifically binds to VEGF with a second binding specificity (anti-ANG2/VEGF antibody) at room temperature for 1 hour. Afterwards, these samples were used as positive controls for/in the depletion step.
B) Depletion Step For depletion of VEGF bound to an anti-ANG2/VEGF antibody a biotinylated anti-idiotypic antibody against the binding specificity which specifically binds to ANG2 (anti-id ANG2 antibody-BI) was bound to magnetic streptavidin coated beads (SA beads) at 10 μg/ml. For each sample, 600 μl SA-Beads were washed and separated from supernatant with a magnetic separator. About 600 μl of an anti-id ANG2 antibody containing solution was mixed with the SA-Beads and incubated for 1 h at room temperature. The excess of unbound antibody was removed by 3-times washing of the beads with a magnetic separator. Afterwards, antibody coated beads were incubated with 250 μl of samples containing complexes of anti-ANG2/VEGF antibody and VEGF. Samples were incubated at room temperature with shaking for 1 hour. After incubation, beads were separated from the sample with a magnetic separator. Supernatant was taken for analysis of "free" VEGF using an ELISA (see Example 2). The remaining beads were transferred into ELECSYS container and bead-bound VEGF (anti-ANG2/VEGF antibody-bound VEGF) was analyzed with ELECSYS 2010 analyzer according to the manufacturer's instructions (see Example 3).

Two different anti-idiotypic antibodies directed against the ANG2 binding specificity were used for depletion of VEGF (see also Example 5):
  i) polyclonal anti-id ANG2 antibody Rb-IgG-BI,
  ii) monoclonal anti-id ANG2 antibody M-2.3.55-BI.

Depletion of Anti-HER3/c-MET Antibody-c-MET Complexes from a Sample

A) Assembly of Complexes of Anti-HER3/c-MET Antibody and c-MET

A constant concentration of c-MET was incubated with increasing amount of bispecific antibody which specifically binds to HER3 with a first binding specificity and which specifically binds to c-MET with a second binding specificity (anti-HER3/c-MET antibody) at room temperature for 1 hour. Afterwards, this sample was treated with beads for depletion of anti-HER3/c-Met antibody-c-MET complexes.

B) Depletion Step

For depletion of c-MET bound to anti-HER3/c-MET antibody a biotinylated anti-idiotypic antibody against the binding specificity which specifically binds to HER3 (anti-id HER3 antibody-BI) was bound to magnetic streptavidin coated beads (SA-beads) at about 10 µg/ml. For each sample, 600 µl SA-Beads were washed and separated from supernatant with a magnetic separator. About 600 µl of an anti-id HER3 antibody M1.1.10-BI comprising solution was mixed with the SA-Beads and incubated for 1 h at room temperature. The excess of unbound antibody was removed by 3-times washing of the beads with a magnetic separator. Afterwards, antibody coated beads were incubated with 250 µl of samples containing complexes of anti-HER3/c-MET antibody and c-MET. Samples were incubated at room temperature with shaking for 1 hour. After incubation, beads were separated from the sample with a magnetic separator. Supernatant was taken for analysis of "free" c-MET in ELISA.

Four anti-idiotypic antibodies directed against the HER3 binding specificity were evaluated for depletion of anti-HER3/c-MET antibody-bound c-MET (see also Example 4):
  i) monoclonal anti-id HER3 antibody M-1.1.10-IgG,
  ii) monoclonal anti-id HER3 antibody M-2.11.123-IgG,
  iii) monoclonal anti-id HER3 antibody M-2.5.45-IgG,
  iv) monoclonal anti-id HER3 antibody M-2.9.55-IgG.

Example 2

Enzyme Linked Immunosorbant Assays

ELISA for Detection of VEGF

A commercial available sandwich immunoassay has been used according to the manufacturers' instructions (R+D Systems Cat# DVE00).

Figure 3:
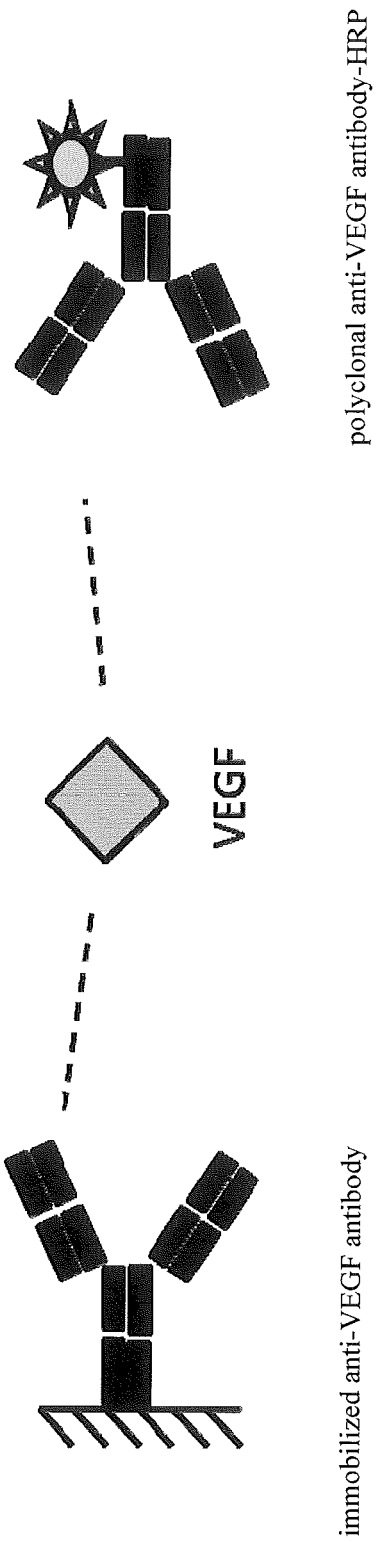
FIG. 3 Sandwich ELISA for detection of VEGF: An immobilized anti-VEGF antibody binds VEGF and another labeled anti-VEGF antibody allows detection of bound VEGF; the assay is used to detect "free" VEGF in the supernatant of a sample after depletion; for detection of c-MET, the same assay format using two anti-c-MET antibodies was applied.

The supernatant sample from the depletion step (see Example 1) was diluted 10-fold and added to the wells of a pre-coated microplate (R+D Systems). Free VEGF contained in the sample was bound by the anti-VEGF antibody coated to wells of the microplate. After 2 hours incubation time at room temperature, unbound sample was removed by 3-times washing of the plate. Afterwards, a polyclonal HRP-linked anti-VEGF antibody (horseradish peroxidase linked anti-VEGF antibody) was added to the wells and incubated for another 2 hours at room temperature. After another washing step, TMB substrate solution was added to the wells. The color reaction was stopped by addition of sulfuric acid prior to measurement (see FIG. 3).

ELISA for Detection of c-MET

A commercial available sandwich immunoassay was used (R+D Systems Cat# DY358).

A mouse monoclonal anti-c-MET antibody was diluted to a working concentration of about 180 µg/ml in phosphate buffered saline (PBS). About 100 µl of this solution was pipetted into each well of a Nunc Maxisorb plate and incubated for 1 hour at room temperature. After coating of the capture antibody to the wells of the plate, the plate was washed 3-times with PBS supplemented with 0.05% (w/v) Tween and blocked with PBS comprising 1% (w/v) bovine serum albumin (BSA) for 1 hour at room temperature. Prior to addition of samples, the plate was washed 3-times with PBS.

Supernatant from depletion step of c-MET (see Example 1) was diluted 10-fold. About 100 µl of each sample dilution as well as a series of diluted calibration standards was pipetted into 2 wells of the coated and blocked microplate each and incubated for 1 hour at room temperature.

Figure 4:
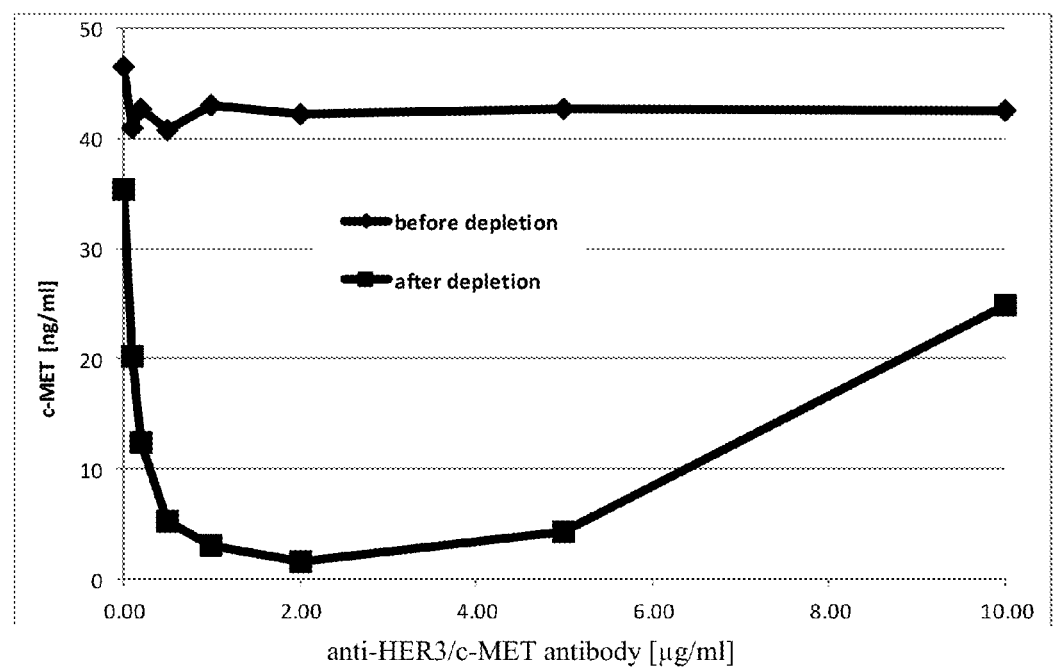
FIG. 4 C-MET levels before and after immuno depletion: Samples with 50 ng/ml c-MET and increasing amount of bispecific anti-HER3/c-MET antibody were depleted of the bispecific antibody with an anti-idiotypic antibody specifically binding to the HER3 binding specificity of the bispecific antibody; the diagram shows c-MET concentration before and after depletion determined by an ELISA; levels of c-MET are similar before depletion independent on the amount of bispecific antibody; by depletion of c-MET-bound to bispecific antibody (drug-bound target) is removed; the detected c-MET (free c-MET) concentration after depletion was about 1 ng/ml in presence of 2 microgram per ml bispecific antibody.

After incubation unbound sample was removed by 3-times washing of the plate. Afterwards, a polyclonal biotin-linked anti-c-MET antibody was added to the wells and incubated for another 2 hours at room temperature. After another washing step, streptavidin-HRP conjugate (R+D systems) was diluted 200-fold and 100 µl of this solution was pipetted into each well of the microplate and incubated for 1 hour at room temperature. After another washing step, TMB substrate solution was added to the wells and color reaction was stopped by addition of sulfuric acid prior to measurement (see FIG. 4).

Example 3

ELECSYS for Detection of Bound Complexes of Antigen X and Anti-X/Y Antibody

The beads used in depletion step (see example 1) were washed and separated with a magnetic separator 3-times in ELECSYS assay buffer to remove unbound substances. Beads from each sample were dissolved in 600 µl ELECSYS assay buffer and taken for analysis.

Briefly 170 µl of the beads were incubated with 10 µl buffer and 20 µl ruthenium labeled antibody against antigen X (15 µg/ml) for 15 minutes. Ruthenium-labeled antibody bound to immobilized complex of antigen X-anti-X/Y antibody-anti idiotypic antibody on SA-Beads was detected (see e.g. Stockmann, W., et al., Wien. Klin. Wochenschr. 110 (1998) Suppl. 3:10-21; Forest, J. C., et al., Clin. Biochem. 31 (1998) 81-88).

Example 4

Evaluation of Anti-Idiotypic Antibodies as Depletion Tools

According to the method as described in Example 1 different anti-idiotypic antibodies with different kinetic constants were used for depletion of anti-HER3/c-MET antibody and complexes thereof.

Assessment of Kinetic Constants of Anti-Idiotypic Antibodies Specifically Binding to the HER3 Binding Specificity of the Anti-HER3/c-MET Antibody by Surface Plasmon Resonance All measurements were performed with the BIAcore® T100 instrument using a CM5-chip. Coating of the chip was achieved by standard amine coupling. Unless otherwise indicated, all incubations were performed in HBS-buffer (HEPES, NaCl, pH 7.4) at 25° C. A saturating amount of a polyclonal goat anti-mouse Fc-gamma antibody was immobilized by amine coupling on one flow cell of the CM5-chip.

Subsequently, the different monoclonal mouse antibodies directed against the anti-HER3/c-MET antibody binding specificity, which specifically binds to HER3, were injected for 60 seconds at a flow rate of 30 µl/min and were bound by the anti-mouse Fc antibody. All animal sera were diluted in HBS buffer. Binding (association) was analyzed by injection of anti-HER3/c-MET antibody for 60 sec. at a flow rate of 30 µl/min. Dissociation was measured by washing the chip surface with HBS buffer for 180 sec. Using BIAevaluation Software from BIAcore® the dissociation constant values ($=k_a$; kd; $K_D$) were calculated with a 1:1 Langmuir fitting model.

TABLE

Kinetic parameters for binding of various anti-idiotypic antibodies against the HER3 binding specificity of the anti-HER3/c-MET antibody determined by SPR-analysis.

| Analyte | ka (1/Ms) | kd (1/s) | KD (M) |
|---|---|---|---|
| monoclonal anti-id HER3 antibody M-1.1.10-IgG | $4.8*10^5$ | $5.4*10^{-5}$ | $1.1*10^{-10}$ |
| monoclonal anti-id HER3 antibody M-2.11.123-IgG | $1.6*10^4$ | $1.0*10^{-3}$ | $6.3*10^{-8}$ |
| monoclonal anti-id HER3 antibody M-2.5.45-IgG | $1.2*10^5$ | $3.4*10^{-4}$ | $2.9*10^{-9}$ |
| monoclonal anti-id HER3 antibody M-2.9.55-IgG | $1.0*10^6$ | $1.1*10^{-3}$ | $1.1*10^{-9}$ |

Figure 5:
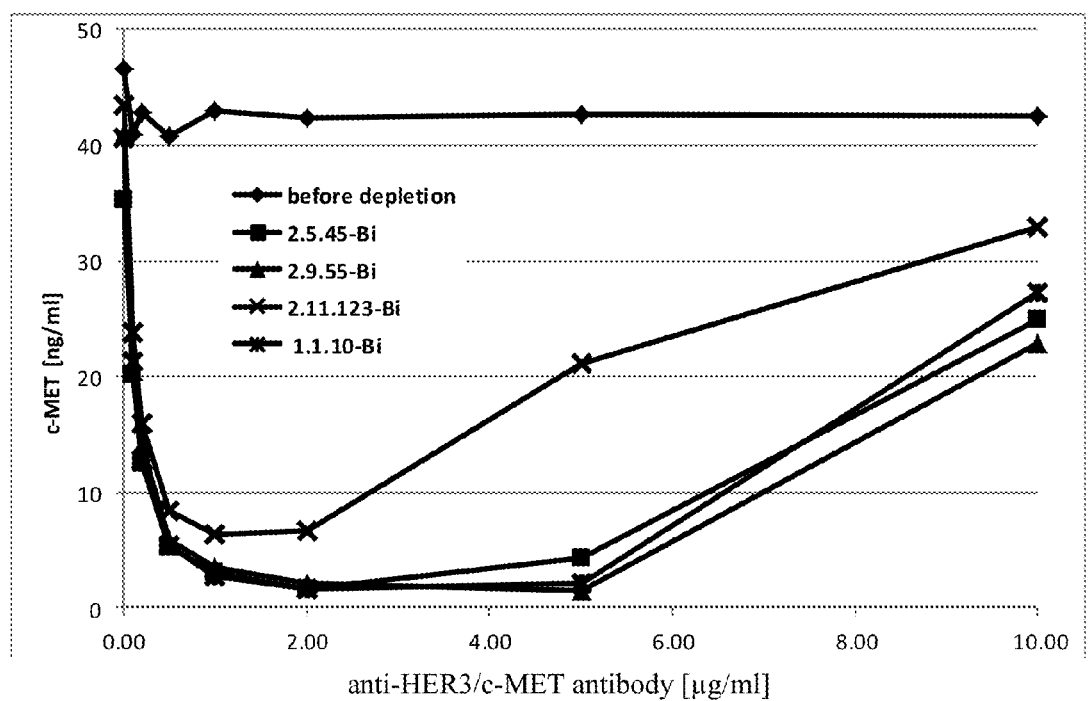
FIG. 5 Comparison of several anti-idiotypic antibodies used for immuno depletion: four anti-idiotypic antibodies specifically binding to the HER3 binding specificity of the bispecific antibody were used for depletion of bispecific antibody-"bound" c-MET; the experiment was carried out as described for FIG. 4; the depletion with antibody M2.11.125 was less efficient than with the three other anti-idiotypic antibodies.
Figure 6:
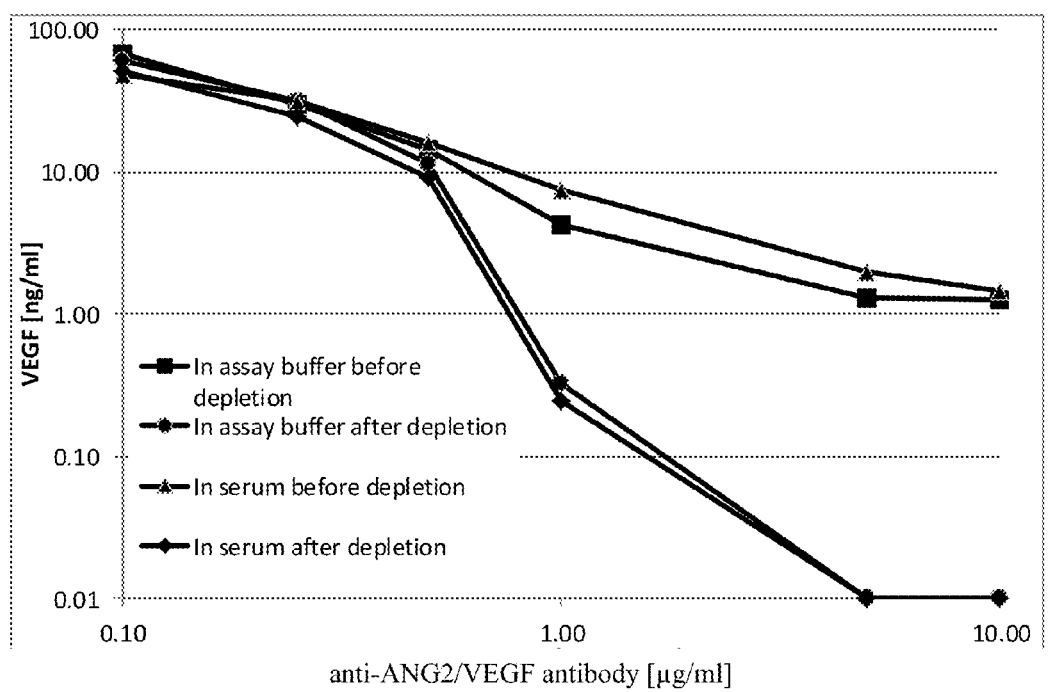
FIG. 6 VEGF amount in the supernatant of buffer and serum samples after depletion, buffer and serum samples with 50 ng/ml VEGF and increasing amount of bispecific anti-ANG2/VEGF antibody were depleted with an anti-idiotypic antibody specifically binding to the ANG2 binding specificity of the bispecific antibody; VEGF concentration before and after immuno depletion were measured by an ELISA (FIG. 3); depletion of drug-bound target in serum/plasma is similar efficient as in assay buffer; the bispecific antibody concentration dependent signal course before depletion is due to the assay format and an epitope overlap on VEGF specifically bound by the multispecific binder and one of the anti-VEGF antibodies used in the assay.
Figure 7:
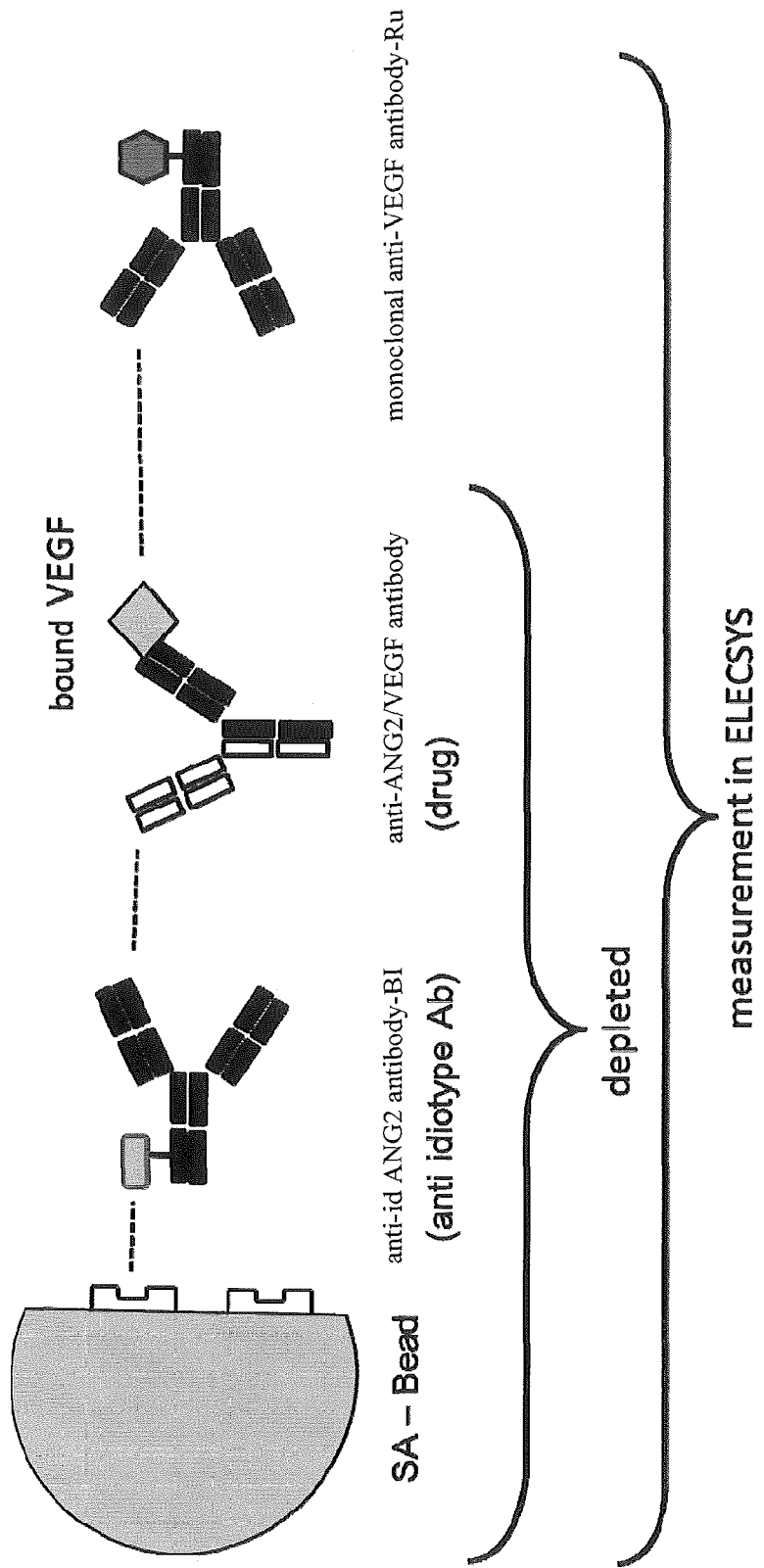
FIG. 7 Detection of drug-bound target after immuno depletion with anti-idiotypic antibodies immobilized on streptavidin beads: separated magnet beads were transferred into an ELECSYS 2010 analyzer; VEGF of bead-bound anti-idiotypic antibody/bispecific antibody/VEGF-complex were detected with a ruthenium-labeled anti-VEGF antibody.

The results are also shown in FIG. 5.

It can be seen from FIG. 5 that the depletion of the anti-HER3/c-Met antibody with monoclonal anti-id HER3 antibody M-2.11.123-IgG is not as effective as with the other antibodies.

Depletion of Drug-Bound c-MET and Detection of Free c-MET

C-MET bound to anti-HER3/c-MET antibody was depleted using anti-idiotypic antibodies as described in Example 1. Supernatant was measured in c-MET ELISA as described in Example 2.

Example 5

Depletion of Drug Bound VEGF in Human Serum and Buffer

According to Example 1 anti-ANG2/VEGF antibody was diluted to 10/5/1/0.5/0.25 and 0 µg/ml and incubated with VEGF at a constant concentration of 50 ng/ml. Dilutions were generated in 2 different matrices:
  Low Cross buffer (Candor Bioscience GmbH, #100500)
  Human Pool Serum (Trina, NHS Base matrix)
Samples were incubated at room temperature for 1 hour. Afterwards, samples were depleted as described in Example 1.

Monoclonal anti-id ANG2 antibody M-2.3.55-BI was used to capture complexes of VEGF with anti-ANG2/VEGF antibody.

After depletion Supernatant was measured in VEGF ELISA as described in Example 2.

The residual VEGF amount of the supernatant after depletion was set in relation to the control sample (50 ng/ml) incubated without any bispecific antibody. The results are shown in the following Table as relative recovery in %.

TABLE

Relative VEGF amount in the supernatant of buffer and serum samples after immuno depletion, set in relation to levels before depletion.

| anti-ANG2/VEGF antibody [µg/ml] | free VEGF in buffer | free VEGF in human serum |
|---|---|---|
| 10.00 | 0% | 0% |
| 5.00 | 0% | 0% |
| 1.00 | 1% | 0% |
| 0.50 | 23% | 18% |
| 0.25 | 63% | 49% |
| 0.00 | 121% | 103% |

Example 6

Assessment of the Influence of Free Antigen Concentration on Depletion Shown with Anti-HER3/c-MET Antibody According to Example 1 depletion of anti-HER3/c-MET antibody bound c-MET was performed in samples containing various concentrations of c-MET. Three different concentrations of c-MET (5, 10, 50 ng/ml) were incubated with increasing amount of anti-HER3/c-MET antibody at room temperature. Incubation was performed for 1 hour and overnight. Afterwards, these samples were depleted of anti-HER3/c-MET antibody-c-MET complexes as described in Example 1.

Results are shown as recovery of c-MET concentrations in each sample from the spiked concentration in the following Tables a and b.

TABLE a

Recovery of c-MET after depletion with one hour incubation time and dependence on concentration of drug (bispecific antibody) and target (antigen).

| anti-HER3/c-MET antibody [µg/ml] | spiked c-MET concentration [ng/ml] | | |
|---|---|---|---|
| | 50 | 10 | 5 |
| 20 | 46% | 42% | 37% |
| 10 | 6% | 4% | 4% |
| 5 | 3% | 3% | 3% |
| 3 | 4% | 5% | 5% |
| 1 | 13% | 11% | 12% |
| 0.5 | 19% | 18% | 17% |
| 0.1 | 48% | 46% | 58% |
| 0 | 58% | 65% | 43% |

TABLE b

Recovery of c-MET after depletion with overnight incubation time and dependence on concentration of drug (bispecific antibody) and target (antigen).

| anti-HER3/c-MET antibody [µg/ml] | spiked c-MET concentration [ng/ml] | | |
|---|---|---|---|
| | 50 | 10 | 5 |
| 20 | 45% | 53% | 46% |
| 10 | 3% | 2% | 2% |
| 5 | 3% | 3% | 3% |

TABLE b-continued

Recovery of c-MET after depletion with overnight incubation time and dependence on concentration of drug (bispecific antibody) and target (antigen).

| anti-HER3/c-MET antibody [µg/ml] | spiked c-MET concentration [ng/ml] | | |
|---|---|---|---|
| | 50 | 10 | 5 |
| 3 | 4% | 4% | 4% |
| 1 | 9% | 10% | 9% |
| 0.5 | 16% | 17% | 15% |
| 0.1 | 43% | 43% | 40% |
| 0 | 59% | 69% | 54% |

Example 7

Influence of VEGF on Depletion

Bispecific anti-ANG2/VEGF antibody was spiked to 500 µl cynomolgus pool plasma at 100 µg/ml. The spiked serum was divided into 5 aliquots with 100 µl each. Each aliquot was spiked with different amounts of VEGF in the range of from 0 ng/ml to 100 ng/ml.

The samples were processed with streptavidin coated magnetic sepharose beads with bound anti-id VEGF antibody M2.45.51-BI. Samples and beads were incubated over night at ambient temperature.

After incubation, the magnetic beads were separated from the sample with a magnetic separation unit.

The level of remaining anti-ANG2/VEGF antibody in the supernatant after bead-treatment/bead based depletion was determined using an ELISA.

In the ELISA, biotinylated VEGF was bound to streptavidin-coated microtiter plates (SA-MTP) in the first step. The excess of unbound VEGF was removed by washing. Samples/standards, e.g. anti-ANG2/VEGF antibody spiked in cynomolgus plasma, were incubated for 1 hour at room temperature. After washing, digoxigenylated monoclonal anti-human-Fcγ pan-antibody R10Z8E9 was used for detection and incubated for 1 hour. After washing the bound digoxingenylated monoclonal anti-human-Fcγ pan-antibody R10Z8E9 was detected with an anti-digoxigenin-antibody horseradish peroxidase (HRP) conjugate. The enzyme conjugate catalyzes the color reaction of ABTS substrate. The signal was measured by ELISA reader at 405 nm wavelength (reference wavelength: 490 nm). Absorbance values of each serum sample were determined in triplicates. The results are shown in the following Table.

TABLE

| VEGF [ng/ml] | bispecific antibody level before depletion [ng/ml] | signal Mw | bispecific antibody level after depletion [ng/ml] | relative remaining antibody level |
|---|---|---|---|---|
| 100.0 | 100000.00 | 0.29 | 106.55 | 0.11% |
| 10.0 | 100000.00 | 0.31 | 114.09 | 0.11% |
| 1.0 | 100000.00 | 0.32 | 120.98 | 0.12% |
| 0.1 | 100000.00 | 0.32 | 119.64 | 0.12% |
| 0.0 | 100000.00 | 0.29 | 107.44 | 0.11% |

As shown in the Table above, the depletion of the bispecific monoclonal antibody is independent of the amount of first antigen (i.e. VEGF as in this example) in the sample. Therefore, it can be concluded that the amount of second antigen has no influence on concentration determination of free first antigen (i.e. free ANG2 as in this example).

Without being bound by this theory robustness to potential interferences by the first antigen can be achieved e.g. i) by using an anti-idiotypic antibody with higher affinity to the bispecific antibody than the affinity of the first antigen to the bispecific antibody, or ii) by using a non-neutralizing anti-idiotypic antibody that does not bind to same part of CDRs as the antigen.

The invention claimed is:

1. An in vitro method for the determination of the presence and/or amount of an antigen of a multispecific antibody in a sample, whereby the antigen to be detected can be specifically bound by a first binding specificity of the multispecific antibody, comprising the steps of:
   incubating the sample comprising the multispecific antibody, multispecific antibody bound antigen and free antigen with an anti-idiotypic antibody that specifically binds to a second binding specificity of the multispecific antibody, which is different from the first binding specificity,
   depleting the anti-idiotypic antibody-multispecific antibody-complex and anti-idiotypic antibody-multispecific antibody-antigen complex from the sample prior to the determination of the presence and/or the amount of free antigen, and
   determining the presence and/or the amount of free antigen in the multispecific antibody-depleted sample.

2. The method according to claim 1, wherein the binding specificity is a binding site or a pair of an antibody heavy chain variable domain and an antibody light chain variable domain.

3. The method according to claim 1, wherein the determining the presence and/or the amount of the antigen comprises the following steps:
   incubating the multispecific antibody-depleted sample with a capture antibody that specifically binds to the antigen to form a capture antibody-antigen complex, and
   correlating the formed capture antibody-antigen complex to the amount of the antigen in the sample.

4. The method according to claim 1, wherein the determining of the amount of the antigen comprises the following steps:
   incubating the multispecific antibody-depleted sample with a capture antibody that specifically binds to the antigen to form a capture antibody-antigen complex,
   incubating the capture antibody-antigen complex with a tracer antibody, whereby the capture antibody and the tracer antibody bind to non-overlapping epitope on the antigen, and
   correlating the formed capture antibody-antigen-tracer antibody complex to the amount of the antigen in the sample.

5. The method according to claim 1, wherein the determining of the amount of the antigen comprises the following steps:
   incubating the multispecific antibody-depleted sample with a capture antibody that specifically binds to the antigen to form a capture antibody-antigen complex,
   incubating the capture antibody-antigen complex with a tracer antibody, whereby the capture antibody and the tracer antibody bind to non-overlapping epitope on the antigen,
   incubating the capture antibody-antigen-tracer antibody complex with a detection antibody comprising a detectable label, whereby the detection antibody specifically binds to the tracer antibody at an epitope outside the variable domains of the tracer antibody, and correlating the formed capture antibody-antigen-tracer antibody complex to the amount of the antigen in the sample.

6. The method according to claim 1, wherein the multispecific antibody is a bispecific antibody, or a trispecific antibody, or a tetraspecific antibody, or a pentaspecific antibody, or a hexaspecific antibody.

7. The method according to claim 1, wherein the multispecific antibody is a bispecific antibody.

8. The method according to claim 1, wherein the multispecific antibody is a bispecific antibody that has a first binding specificity that specifically binds to a first antigen or first epitope on an antigen and that has a second binding specificity that specifically binds to a second antigen or to a second epitope on the antigen.

9. The method according to claim 1, wherein the method comprises the following steps:

incubating the sample comprising antigen and multispecific antibody with an anti-idiotypic antibody that specifically binds to a second binding specificity of the multispecific antibody which is different from the first binding specificity, to form an anti-idiotypic antibody-multispecific antibody complex, removing the anti-idiotypic antibody-multispecific antibody complex from the sample, and determining the amount of the antigen in the multispecific-antibody depleted sample.

10. The method according to claim 1, wherein the anti-idiotypic antibody has an association constant $k_a$ of $10^5$ l/mol/s or more to the second binding specificity of the multispecific antibody.

11. The method according to claim 1, wherein the anti-idiotypic antibody has a $K_D$ value of $5*10^{-8}$ mol/l or less for the binding to the second binding specificity of the multispecific antibody.

12. The method according to claim 1, wherein the incubating with the anti-idiotypic antibody is for about 10 minutes to about 36 hours.

13. The method according to claim 1, wherein the sample is adjusted to a multispecific antibody concentration of about 2 µg/ml to about 15 µg/ml.

14. The method according to claim 1, wherein the sample is adjusted to a total antigen concentration of from about 1 ng/ml to about 250 ng/ml.

15. The method according to claim 1, wherein the anti-idiotypic antibody is bound or conjugated to a solid phase.

16. The method according to claim 1, wherein the anti-idiotypic antibody is conjugated (immobilized) via a specific binding pair.

17. The method according to claim 16, wherein the binding pair (first component/second component) is selected from streptavidin or avidin/biotin, antibody/antigen, lectin/polysaccharide, steroid/steroid binding protein, hormone/hormone receptor, enzyme/substrate, IgG/Protein A and/or G.

18. The method according to claim 16, wherein the anti-idiotypic antibody is conjugated to biotin and immobilization is performed via immobilized avidin or streptavidin.

19. The method according to claim 1, wherein the anti-idiotypic antibody is biotinylated and the solid phase is streptavidin coated.

20. The method according to claim 1, wherein the anti-idiotypic antibody is a biotinylated anti-idiotypic antibody against the multispecific antibody and is conjugated to a solid phase via streptavidin.

21. The method according to claim 1, wherein the solid phase is a streptavidin coated paramagnetic bead or a streptavidin coated sepharose bead.

22. The method according to claim 1, wherein the anti-idiotypic antibody is a mixture comprising at least two anti-idiotypic antibodies that differ in the antibody site at which they are conjugated to the solid phase.

23. The method according to claim 1, wherein the anti-idiotypic antibody mixture comprises the anti-idiotypic antibody conjugated via at least two different amino groups to the solid phase.

24. The method according to claim 1, wherein the conjugation of the anti-idiotypic antibody to its conjugation partner is performed by chemically binding via N-terminal and/or ϵ-amino groups (lysine), and/or ϵ-amino groups of different lysines, carboxy-, sulfhydryl-, hydroxyl- and/or phenolic functional groups of the amino acid backbone of the drug antibody, and/or sugar alcohol groups of the carbohydrate structure of the drug antibody.

25. The method according to claim 15, wherein the anti-idiotypic antibody is conjugated to the solid phase by passive adsorption.

26. The method according to claim 1, wherein the sample comprises multispecific antibody, free antigen and multispecific antibody-antigen complexes and the detection is of free antigen of the multi specific antibody.

* * * * *